US012649703B2

(12) United States Patent
Chmura et al.

(10) Patent No.: US 12,649,703 B2
(45) Date of Patent: Jun. 9, 2026

(54) PROCESSES FOR SYNTHESIZING PARAXYLENE AND CATALYST FOR SAME

(71) Applicant: UOP LLC, Des Plaines, IL (US)

(72) Inventors: Steven L. Chmura, Schiller Park, IL (US); Erin M. Broderick, Arlington Heights, IL (US); Gregory B. Kuzmanich, Arlington Heights, IL (US); Jaime G. Moscoso, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 48 days.

(21) Appl. No.: 18/459,612

(22) Filed: Sep. 1, 2023

(65) Prior Publication Data

US 2024/0208883 A1     Jun. 27, 2024

Related U.S. Application Data

(60) Provisional application No. 63/477,097, filed on Dec. 23, 2022.

(51) Int. Cl.
| | |
|---|---|
| *C07C 2/86* | (2006.01) |
| *B01J 21/12* | (2006.01) |
| *B01J 29/70* | (2006.01) |
| *B01J 37/28* | (2006.01) |
| *C07C 2/02* | (2006.01) |
| *C07C 2/50* | (2006.01) |
| *C07C 2/52* | (2006.01) |

(52) U.S. Cl.
CPC .............. *C07C 2/865* (2013.01); *B01J 21/12* (2013.01); *B01J 29/7007* (2013.01); *B01J 37/28* (2013.01); *C07C 2/50* (2013.01); *C07C 2/52* (2013.01); *C07C 2/02* (2013.01); *C07C 2/86* (2013.01); *C07C 2529/85* (2013.01)

(58) Field of Classification Search
CPC .. C07C 2/865; C07C 2/50; C07C 2/52; C07C 2/02; C07C 2/86; C07C 2529/85; C07C 2529/70; C07C 2/862; B01J 21/12; B01J 29/7007; B01J 37/28; B01J 29/40
See application file for complete search history.

(56) References Cited

U.S. PATENT DOCUMENTS

| 7,572,925 B2 | 8/2009 | Dumesic et al. |
|---|---|---|
| 8,314,267 B2 | 11/2012 | Brandvold |

(Continued)

FOREIGN PATENT DOCUMENTS

WO       2018064604 A1     4/2018

OTHER PUBLICATIONS

Cecilia Manrique et al., Phosphorous-Modified Beta Zeolite and Its Performance in Vacuum Gas Oil Hydrocracking Activity, Energy Fuels, 2019, 33, 3483-3491.

(Continued)

*Primary Examiner* — Ali Z Fadhel

(57) ABSTRACT

Processes and a catalyst for the cycloaddition of an olefin, such as C2 to C4 olefins like, ethylene, propylene and butylene, to a biomass derived compound, such as dimethylfuran, furan, methylfuran. The catalyst has a relatively low silica to alumina ratio of around 25 compared with conventional catalysts which have a ratio greater than 1000. The catalyst has phosphorus and may be a beta zeolite. Such a catalyst can be used to generate a high yield of bio-based para-xylene.

15 Claims, 3 Drawing Sheets

(56)           References Cited

U.S. PATENT DOCUMENTS

| | | |
|---|---|---|
| 9,260,359 B2 | 2/2016 | Masuno et al. |
| 9,772,515 B2 | 9/2017 | Wehlus et al. |
| 10,125,060 B2 | 11/2018 | Masuno et al. |
| 10,392,317 B2 | 8/2019 | Masuno et al. |
| 2010/0331568 A1 | 12/2010 | Brandvold |
| 2019/0344252 A1 | 11/2019 | Cho et al. |
| 2021/0253495 A1* | 8/2021 | Parvulescu ............. C07C 2/865 |

OTHER PUBLICATIONS

Chun-Chih Chang et al., Lewis acid zeolites for tandem Diels-Alder cycloaddition and dehydration of biomass-derived dimethylfuran and ethylene to renewable p-xyelene, Green Chem., 2016, 18, 1368.
Janardhan L. Hodala et al, Enhancement in activity and shape selectivity of zeolite BEA by phosphate treatment for 2-methoxynaphthalene acylation, RSC Adv., 2016, 6, 90579.
Saikat Dutta et al., Novel Pathways to 2,5-Dimethylfuran via Biomass-Derived 5-(Chloromethyl)furfural, ChemSusChem, 2014, 7, 3028-3030.
Hong Je Cho et al., Renewable p-Xylene from 2,5-Dimethylfuran and Ethylene Using Phosphorus-Containing Zeolite Catalysts, ChemCatChem, 2017, 9, 398-402.

Jingye Yu et al., Adsorption and reaction properties of SnBEA, ZrBEA and H-BEA for the formation of p-xylene from DMF and ethylene, Catal. Sci. Technol., 2016, 6, 5729.
Electronic Supplementary Material for Catalysis Science and Technology, The Royal Society of Chemistry, 2016.
Anh Tuan Hoang et al., Catalyst-Based Synthesis of 2,5-Dimethylfuran from Carbohydrates as a Sustainable Biofuel Production Route, ACS Sustainable Chem. Eng. 2022, 10, 3079-3115.
Mark Mascal, 5-(Chloromethyl)furfural (CMF): A Platform for Transforming Cellulose into Commercial Products, ACS Sustainable Chem. Eng., 2019, 7, 5588-5601.
Jing Luo et al, Comparison of HMF hydrodeoxygenation over different metal catalysts in a continuous flow reactor, Applied Catalysis A: General 508 (2015) 86-93.
International Search Report from corresponding PCT application No. PCT/US2023/084494, mailed Apr. 24, 2024.
Written Opinion from corresponding PCT application No. PCT/US2023/084494, mailed Apr. 24, 2024.
Zhao, R. et al., Renewable p-xylene synthesis via biomass-derived 2, 5-dimethylfuran and ethanol by phosphorous modified H-Beta zeolite, Microporous and Mesoporous Materials, Mar. 3, 2022, vol. 334, Article No. 111787, pp. 1-9.

* cited by examiner

PROCESSES FOR SYNTHESIZING PARAXYLENE AND CATALYST FOR SAME

RELATED APPLICATIONS

This application claims priority to U.S. Patent Application Ser. No. 63/477,097 filed on Dec. 23, 2022, the entirety of which is incorporated herein by reference.

FIELD OF THE INVENTION

This invention relates generally to the production of aromatic hydrocarbons from biomass derived compounds and more specifically to overall bio-based pathways for making para-xylene from carbohydrates such as hexoses (e.g., glucose or fructose).

BACKGROUND OF THE INVENTION

C8 alkylaromatic hydrocarbons are generally considered to be valuable products, with a high demand for para-xylene. For example, para-xylene is used to commercially synthesize terephthalic acid, a raw material in the manufacture of polyester fabrics.

Major sources of para-xylene include mixed xylene streams that result from the refining of crude oil. Examples of such streams are those resulting from commercial xylene isomerization processes or from the separation of C8 alkylaromatic hydrocarbon fractions derived from a catalytic reformate by liquid-liquid extraction and fractional distillation. The para-xylene may be separated from a para-xylene-containing feed stream, usually containing a mixture of all three xylene isomers, by crystallization and/or adsorptive separation.

Thus, most para-xylene is produced from petroleum-based feedstocks. However, producing para-xylene from petroleum-based feedstocks maintains reliance on refining petroleum and creates greenhouse gas emissions. A biobased para-xylene replacement from renewable feedstock would lower greenhouse gas (GHG) emissions and reduce reliance on petroleum resources. Not being bound by any theory, it is believed that bio-para-xylene may be carbon negative.

More recently, it has been suggested that para-xylene can be produced from a biomass derived component. For example, producing para-xylene from sustainable sugar derived furans such as dimethylfuran (DMF) provides an alternative route to traditional petroleum-based production.

Accordingly, there is an ongoing need and desire to improve the processes which produce para-xylene from a biomass-derived compound.

SUMMARY OF THE INVENTION

This invention describes using a new catalyst for the cycloaddition of an olefin, such as C2 to C4 olefins like, ethylene, propylene and butylene, to a biomass derived compound, such as dimethylfuran, furan, methylfuran. The catalyst has a relatively low silica to alumina ratio of around 25 compared with conventional catalysts which have a ratio greater than 1000. The catalyst has phosphorus and may be 12 membered ring zeolite such as a beta zeolite. Such a catalyst can be used to generate a high yield of bio-based pX.

Advantageously, the DMF starting material for the processes may be synthesized from carbohydrates, thereby providing a production route to para-xylene that relies at least partly on renewable feedstocks and is formed from a biomass derived component.

Therefore, the present invention may be characterized, in at least one aspect, as providing a process for a cycloaddition of an olefin to a biomass derived compound by: contacting an olefin and a biomass derived compound with a catalyst. The catalyst includes a silicon and aluminum in a ratio of less than 1000:1, and further includes phosphorus.

The catalyst may be a beta zeolite.

The ratio of silicon and aluminum may be between 1:1 to 500:1, or between 1:1 to 25:1.

The catalyst may include between 0.001 wt % to 10 wt % phosphorus.

The present invention may also be characterized, broadly, as providing a process for producing para-xylene by: providing an olefin; providing a compound derived from a biomass; and, contacting the olefin and the compound derived from the biomass in the presence of a catalyst. The catalyst includes silicon and aluminum in a ratio of less than 1000:1 and further includes phosphorus.

A molar ratio of the olefin to the compound derived from the biomass may be in a range from 1:100 to 100:1.

A weight ratio of catalyst to the compound derived from the biomass may be in a range from 0.001:1 to 10:1.

The contacting may occur at a temperature in a range of 100 to 500° C.

The contacting may occur at a pressure in a range of 689 to 17,237 kPa (100 to 2,500 psig).

The process may be a continuous process or a batch process.

The catalyst may be a beta zeolite.

The ratio of silicon and aluminum of the catalyst may be between 1:1 to 500:1, or between 1:1 to 25:1.

The catalyst may include between 0.001 wt % to 10 wt % phosphorus.

The present invention may further be generally characterized, in at least one aspect, as providing a catalyst for converting biomass derived compounds to aromatics with an olefin. The catalyst includes a porous support formed from silicon and aluminum in a ratio of less than 100:1 and phosphorus.

The catalyst may be a beta zeolite.

The ratio of silicon and aluminum may be between 1:1 to 25:1.

The catalyst may include between 0.001 wt % to 10 wt % phosphorus.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

Figure 1:
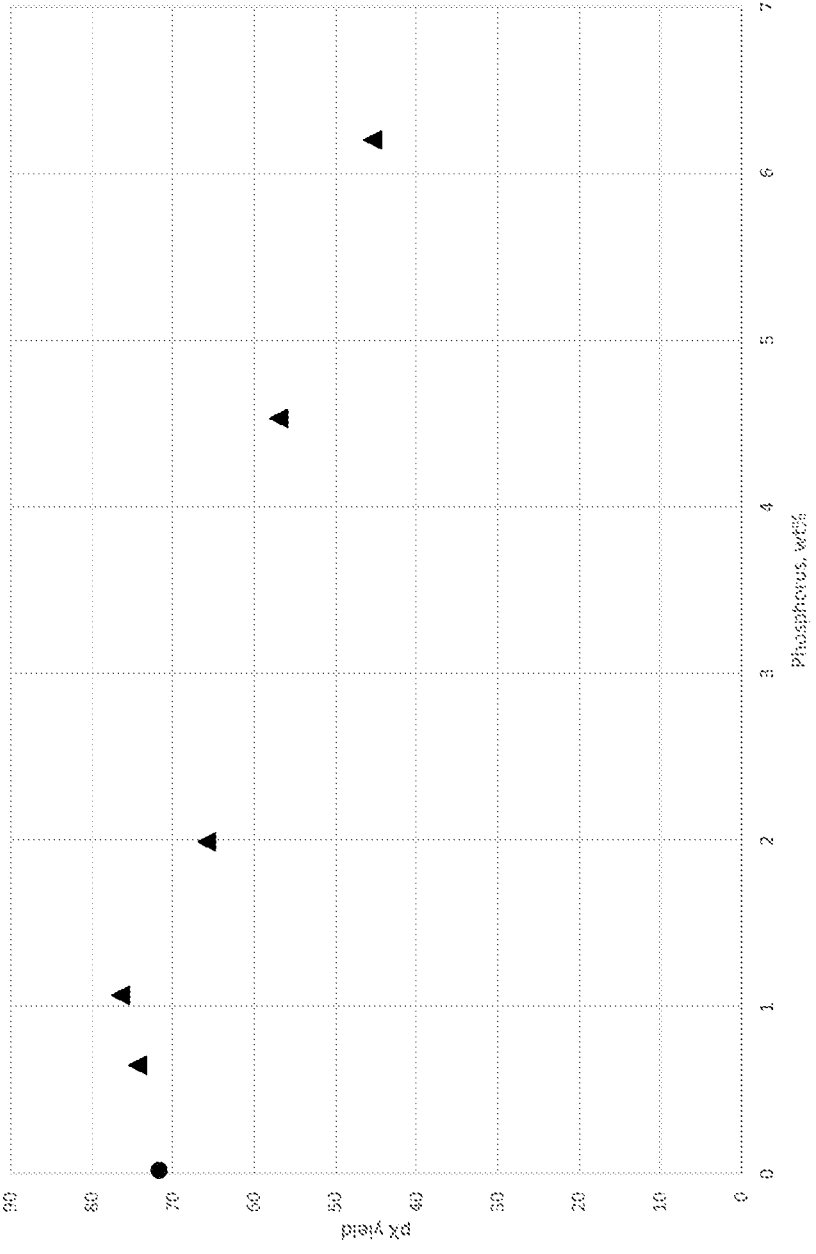
FIG. 1 is a graph showing para-xylene yield compared with phosphorus amount for a conventional catalyst and new catalyst according to one or more aspects of the present invention.

As mentioned above, the present invention is directed to producing aromatic hydrocarbons, and particularly, para-xylene from with a biomass derived component. In the present invention a new catalytic material is provided.

With these general principles in mind, one or more embodiments of the present invention will be described with the understanding that the following description is not intended to be limiting.

As used herein "biomass" includes, but is not limited to, lignin, plant parts, fruits, vegetables, plant processing waste, wood chips, chaff, grain, grasses, corn, corn husks, weeds, aquatic plants, hay, paper, paper products, recycled paper and paper products, and any cellulose, lignin, or combinations thereof containing biological material or material of biological origin.

In known manner the biomass may be used to produce an aromatic compound like furan, methyl furan, dimethylfuran, and in particular, 2,5-dimethylfuran (DMF). See, for example, U.S. Pat. Nos. 7,572,925 and 8,772,515.

The biomass derived components are reacted with an olefin, in particular a C2 to C4 olefin in the presence of a catalyst. According to the present invention, the includes a sporous support including silica and alumina and have a silicon to aluminum in a ratio of less than 1000:1, in particular between 1:1 to 500:1, or 100:1, or 25:1. The support may be a zeolite, such as a 12 membered ring zeolite, and in particular a beta zeolite.

The catalyst further includes phosphorus. Specifically, the catalyst includes between 0.001 wt % to 10 wt % phosphorus, or even between 0.01 to 10 wt % phosphorus. The addition of the phosphorus reduces the number of weak acid cites of the catalyst. However, such a catalyst provides a suitable catalyst with yields that make the production efficient and effective.

An ammonia TPD analysis was performed on a conventional, non-phosphated catalyst, as well as catalyst according to the present disclosure having varying amounts phosphorus. The results of the ammonia TBD are shown below in TABLE 1.

TABLE 1

| | Conven'l Catalyst | New Catalyst | New Catalyst | New Catalyst | New Catalyst | New Catalyst |
|---|---|---|---|---|---|---|
| Phosphorus ICP (mass %) | 0.02 | 6.20 | 4.53 | 1.99 | 1.07 | 0.65 |
| umol/gram 1, umol/gram | 709 | 173 | 304 | 171 | 207 | 263 |
| Peak T1, ° C. | 287 | 254 | 352 | 260 | 262 | 257 |
| μmol/gram 2, μmol/gram | | | | 306 | 411 | 355 |
| Peak T2, ° C. | | | | 377 | 366 | 345 |
| Total number of acid sites | 709 | 173 | 304 | 477 | 618 | 618 |

As demonstrated by the data in TABLE 1, the addition of the phosphorus reduced the number of acid sites.

The reaction of biomass derived compound and the olefin proceeds in the presence of the catalyst as discussed above under suitable cycloaddition reaction conditions. A molar ratio of olefins to biomass derived compound may be in a range between 1:100 to 100:1, or between 1:50 to 50:1, or between 1:10 to 10:1, or between 1:1 to 2:1. A weight ratio of catalyst to the biomass derived compound may be in a range of 0.001:1 to 10:1, or between 0.01:1 to 10:1.

One or more of the reactants may be in another liquid, such as a hydrocarbon oil.

Exemplary temperatures in the reactor or reaction zone in which the catalyst is disposed (e.g., in a batch reactor or as a fixed or moving bed in a continuous reaction system) are in the range from about 100 to 500, or between 200° C. (212° F.) to about 300° C. (572° F.), and often from about 150° C. (302° F.) to about 225° C. (437° F.). Favorable cycloalkylation reaction conditions also include a reaction pressure between 689 kPa to 17,237 kPa (100 to 2,500 psig), or between 1,379 kPa to 13,790 kPa (200 to 2,000 psig).

Whether the reaction is carried out batchwise or continuously, the cycloaddition reaction conditions also generally include a reactor residence time in the range from about 0.1 second to about 48 hours, or from about 3 hours to about 30 hours, or from 6 to 10 hours. The reactor residence time may depend on multiple factors including, in the case of a continuous process in which unconverted/unreacted reactants are recycled to provide a relatively high overall conversion, even if the per-pass conversion is significantly less. The biomass derived compound may be continuously fed to a cycloaddition reaction zone, for example, at a liquid hourly space velocity (LHSV) from about 0.05 hr$^{-1}$ to about 5 hr$^{-1}$. As is understood in the art, the Liquid Hourly Space Velocity (LHSV, expressed in units of hr$^{-1}$) is the volumetric liquid flow rate over the catalyst bed divided by the bed volume and represents the equivalent number of catalyst bed volumes of liquid processed per hour. The LHSV is therefore closely related to the inverse of the reactor residence time.

In an exemplary continuous process, the reactants are continuously fed to one or more reactors containing a catalyst which may be a CSTR type reactor (stirred tank) or which includes a fixed bed of the catalyst (e.g., in a swing-bed reactor system having multiple fixed bed reactors), and a product comprising the converted para-xylene is continuously withdrawn together with unconverted reactants and reaction byproducts such as 2,5-hexanedione. The unconverted materials are preferably separated, for example, based on differences in their relative volatility using one or more separation operations (e.g., flash separation or distillation) employing a single stage or multiple stages of vapor-liquid equilibrium contacting. In some cases, it may be desirable to convert 2,5-hexanedione, which is a hydration byproduct of DMF, back to DMF to improve product yields.

Additionally, unreacted components may be recycled back to the feed, without or without additional drying to remove water. The drying or reduction of water content, for at least the recycle, will reduce the formation of hexanedione and reduce side reactions cause by the presence of water during the dehydration reaction. Drying may be performed via distillation or a molecular sieve.

Aspects of the present invention are therefore directed to methods for producing para-xylene, which include the catalytic cycloaddition of ethylene to DMF and thereby advantageously allow for the use of a carbohydrate and particularly a hexose (e.g., glucose or fructose) as a starting material. In particular, the DMF may be obtained from the conversion of the hexose to HMF, followed by the hydrogenation of HMF to DMF. At least 6 of the carbon atoms of the para-xylene (i.e., those originating from the hexose) may therefore be derived from a renewable feedstock. Moreover, the use of biomass-derived ethanol as a source of feed ethylene can render the entire para-xylene molecule as originating from "green" sources. Particular processes for producing para-xylene, as described herein, therefore include converting a hexose such as glucose or fructose to HMF, hydrogenating the HMF to DMF, and reacting the DMF with ethylene under cycloaddition reaction conditions and in the presence of a catalyst to produce the para-xylene. Further processes according to invention include these features as well as the additional element of oxidizing the para-xylene with oxygen to produce terephthalic acid, a precursor of valuable materials that are, to date, produced commercially only from petroleum-based sources.

Experiments

Figure 2:
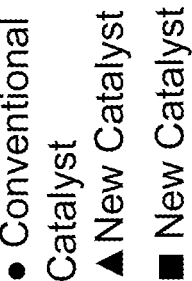
FIG. 2 is a graph showing para-xylene selectivity compared with DMF conversion for a conventional catalyst and new catalyst according to one or more aspects of the present invention; and, FIG. 3 is a graph showing para-xylene selectivity compared with DMF conversion for a conventional catalyst and new catalyst according to one or more aspects of the present invention.
Figure 2:
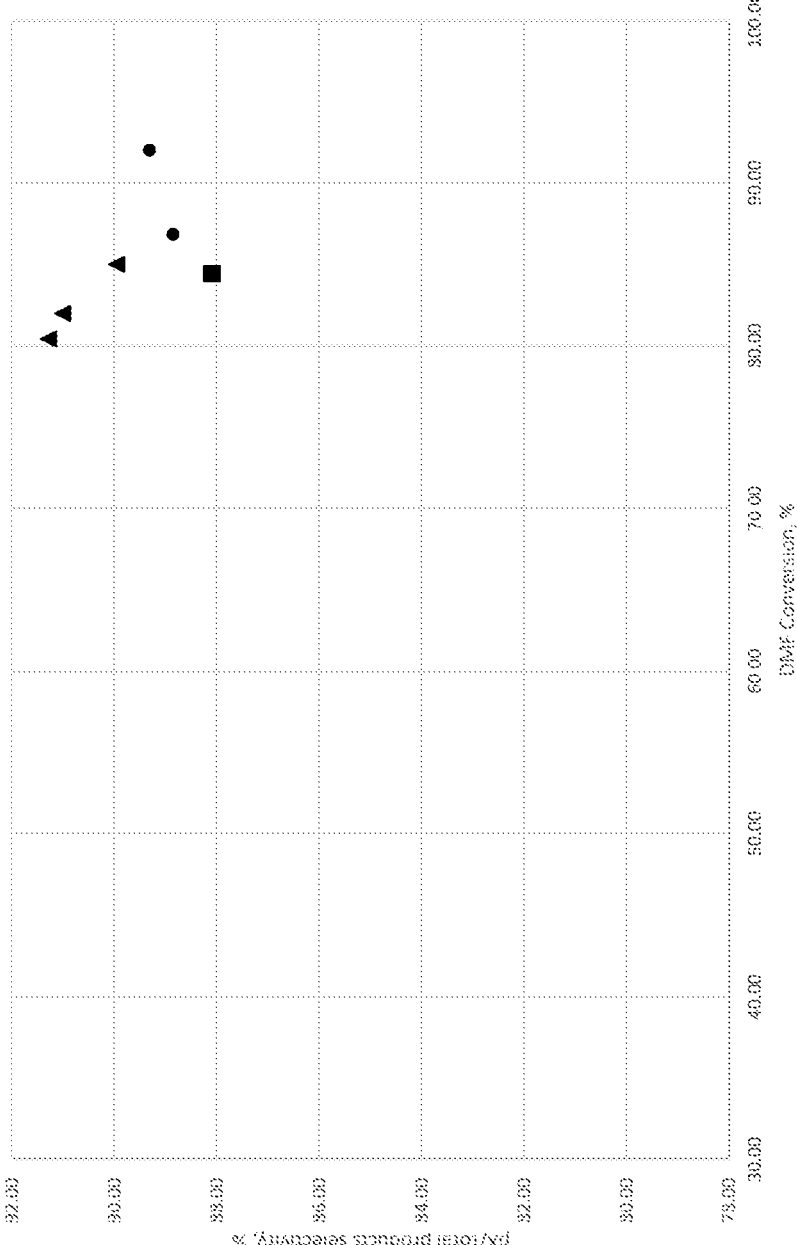

In a batch process, 12 wt % of DMF in octane was reacted with ethylene (1.62 mole ratio of ethylene:DMF) at 285° C. for 6 hours in the presence of a phosphorus containing beta zeolite to generate para-xylene. As shown in the attached FIG. 1, the addition of phosphorus provided similar para-xylene yield that were similar a conventionally used catalyst that does not include phosphorus. As shown in FIG. 2, under these conditions, the new catalyst showed increase selectivity towards para-xylene. The new catalyst in FIG. 2 had 1 wt % phosphorus, except for the catalyst indicated by a different symbol-which contained less that 1 wt % phosphorus.

Figure 3:
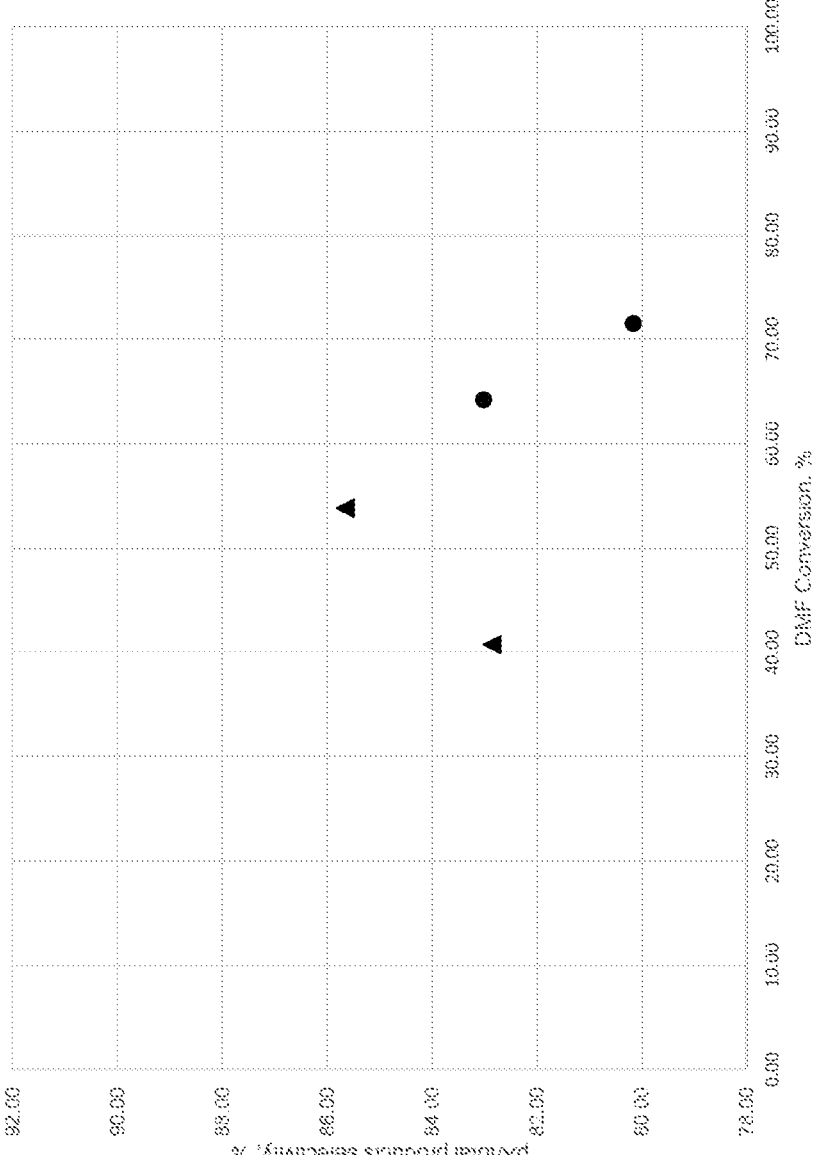

In another process, DMF was reacted was reacted with ethylene (1.0 mole ratio of ethylene:DMF) at 250° C. for 6 hours in the presence of a phosphorus containing beta zeolite to generate para-xylene. As shown in the attached FIG. 3, the new catalyst again showed an increased selectivity towards producing para-xylene.

In the foregoing, to calculate conversion and selectivity, HDO was considered as unreacted DMF in the product due to the equilibrium hydration/dehydration reaction of DMF and HDO. The following equations were used:

$$\text{Conversion (\%)} = \qquad\qquad\qquad\qquad [\text{EQ. 1}]$$
$$100 - \frac{(C \text{ unconverted } DMF \text{ (wt\%)} + C \text{ } HDO \text{ (wt\%)})}{C \text{ Reactant } DMF \text{ (wt\%)}} \times 100$$

$$pX \frac{\text{selectivity}}{\text{total}} \text{products (\%)} = \qquad\qquad [\text{EQ. 2}]$$
$$\frac{C \text{ Product species (wt\%)}}{\Sigma \text{ uncovered reactants in product} + C \text{ } HDO}$$

$$pX \text{ yield} = \frac{(DMF \text{ conversion (\%)} \times \qquad [\text{EQ. 3}]}{pX \text{ selectivity/total products (\%))}}{100}$$

Specific Embodiments

While the following is described in conjunction with specific embodiments, it will be understood that this description is intended to illustrate and not limit the scope of the preceding description and the appended claims.

A first embodiment of the invention is a process for a cycloaddition of an olefin to a biomass derived compound, the process comprising contacting an olefin and a biomass derived compound with a catalyst, the catalyst comprising a silicon and aluminum in a ratio of less than 1000:1, wherein the catalyst further comprises phosphorus. An embodiment of the invention is one, any or all of prior embodiments in this paragraph up through the first embodiment in this paragraph, wherein the catalyst comprises a beta zeolite. An embodiment of the invention is one, any or all of prior embodiments in this paragraph up through the first embodiment in this paragraph, wherein the ratio of silicon and aluminum is between 1:1 to 500:1. An embodiment of the invention is one, any or all of prior embodiments in this paragraph up through the first embodiment in this paragraph, wherein the ratio of silicon and aluminum is between 1:1 to 25:1. An embodiment of the invention is one, any or all of prior embodiments in this paragraph up through the first embodiment in this paragraph, wherein the catalyst comprises between 0.001 wt % to 10 wt % phosphorus.

A second embodiment of the invention is a process for producing para-xylene, the process comprising providing an olefin; providing a compound derived from a biomass; contacting the olefin and the compound derived from the biomass in the presence of a catalyst, the catalyst comprising a silicon and aluminum in a ratio of less than 1000:1, wherein the catalyst further comprises phosphorus. An embodiment of the invention is one, any or all of prior embodiments in this paragraph up through the second embodiment in this paragraph, wherein a molar ratio of the olefin to the compound derived from the biomass is in a range from 1:100 to 100:1. An embodiment of the invention is one, any or all of prior embodiments in this paragraph up through the second embodiment in this paragraph, wherein a weight ratio of catalyst to the compound derived from the biomass is in a range from 0.001:1 to 10:1. An embodiment of the invention is one, any or all of prior embodiments in this paragraph up through the second embodiment in this paragraph, wherein the contacting takes places at a temperature in a range of 100 to 500° C. An embodiment of the invention is one, any or all of prior embodiments in this paragraph up through the second embodiment in this paragraph, wherein the contacting takes places at a pressure in a range of 689 to 17,237 kPa (100 to 2,500 psig). An embodiment of the invention is one, any or all of prior embodiments in this paragraph up through the second embodiment in this paragraph, wherein the process is a continuous process. An embodiment of the invention is one, any or all of prior embodiments in this paragraph up through the second embodiment in this paragraph, wherein the process is a batch process. An embodiment of the invention is one, any or all of prior embodiments in this paragraph up through the second embodiment in this paragraph, wherein the catalyst comprises a beta zeolite. An embodiment of the invention is one, any or all of prior embodiments in this paragraph up through the second embodiment in this paragraph, wherein the ratio of silicon and aluminum is between 1:1 to 500:1. An embodiment of the invention is one, any or all of prior embodiments in this paragraph up through the second embodiment in this paragraph, wherein the ratio of silicon and aluminum is between 1:1 to 25:1. An embodiment of the invention is one, any or all of prior embodiments in this paragraph up through the second embodiment in this paragraph, wherein the catalyst comprises between 0.001 wt % to 10 wt % phosphorus.

A third embodiment of the invention is a catalyst for converting biomass derived compounds to aromatics with an olefin, the catalyst comprising a porous support formed from silicon and aluminum in a ratio of less than 100:1; and, phosphorus. An embodiment of the invention is one, any or all of prior embodiments in this paragraph up through the third embodiment in this paragraph, wherein the catalyst comprises a beta zeolite. An embodiment of the invention is one, any or all of prior embodiments in this paragraph up through the third embodiment in this paragraph, wherein the ratio of silicon and aluminum is between 1:1 to 25:1. An embodiment of the invention is one, any or all of prior embodiments in this paragraph up through the third embodiment in this paragraph, wherein the catalyst comprises between 0.001 wt % to 10 wt % phosphorus.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for a cycloaddition of an olefin to a biomass derived compound, the process comprising:
    contacting an olefin and a biomass derived compound with a catalyst, wherein a molar ratio of the olefin to the biomass derived compound is in a range from 3:2 to 100:1,
    the catalyst comprising a silicon and aluminum in a ratio of less than 1000:1, wherein the catalyst further comprises phosphorus.

2. The process of claim 1, wherein the catalyst comprises a beta zeolite.

3. The process of claim 1, wherein the ratio of silicon and aluminum is between 1:1 to 500:1.

4. The process of claim 1, wherein the ratio of silicon and aluminum is between 1:1 to 25:1.

5. The process of claim 1, wherein the catalyst comprises between 0.001 wt % to 10 wt % phosphorus.

6. A process for producing para-xylene, the process comprising:
    providing an olefin;
    providing a compound derived from a biomass; and,
    contacting the olefin and the compound derived from the biomass in the presence of a catalyst, wherein a molar ratio of the olefin to the compound derived from the biomass is in a range from 3:2 to 100:1, the catalyst comprising a silicon and aluminum in a ratio of less than 1000:1, wherein the catalyst further comprises phosphorus.

7. The process of claim 6, wherein a weight ratio of catalyst to the compound derived from the biomass is in a range from 0.001:1 to 10:1.

8. The process of claim 6, wherein the contacting takes places at a temperature in a range of 100 to 500° C.

9. The process of claim 6, wherein the contacting takes places at a pressure in a range of 689 to 17,237 kPa (100 to 2,500 psig).

10. The process of claim 6, wherein the process is a continuous process.

11. The process of claim 6, wherein the process is a batch process.

12. The process of claim 6, wherein the catalyst comprises a beta zeolite.

13. The process of claim 6, wherein the ratio of silicon and aluminum is between 1:1 to 500:1.

14. The process of claim 6, wherein the ratio of silicon and aluminum is between 1:1 to 25:1.

15. The process of claim 6, wherein the catalyst comprises between 0.001 wt % to 10 wt % phosphorus.

\* \* \* \* \*